United States Patent
Durand

[19]
[11] Patent Number: 6,079,980
[45] Date of Patent: Jun. 27, 2000

[54] DENTAL PATIENT FACE MASK

[76] Inventor: Cecile M. Durand, 22 Almond Pass, Ocala, Fla. 34472

[21] Appl. No.: 09/229,785

[22] Filed: Jan. 11, 1999

[51] Int. Cl.[7] .............................. A61C 5/14; A61D 13/00
[52] U.S. Cl. ................................... 433/137; 2/9; 128/857; 128/206.13
[58] Field of Search .................................. 433/137, 136; 2/9, 173; 128/857, 206.13, 206.18, 206.21, 207.13

[56] References Cited

U.S. PATENT DOCUMENTS

| | | |
|---|---|---|
| 160,844 | 3/1875 | Schwarz . |
| 772,273 | 10/1904 | Braverman . |
| 1,582,164 | 4/1926 | Burstyn . |
| 1,584,012 | 5/1926 | Cocroft . |
| 2,494,406 | 1/1950 | Reitano . |
| 2,564,952 | 8/1951 | Blasius .......................................... 2/11 |
| 3,310,812 | 3/1967 | Gaisser . |
| 3,478,432 | 11/1969 | Gross . |
| 4,050,457 | 9/1977 | Davidson . |
| 4,095,290 | 6/1978 | O'Brien ........................................... 2/9 |
| 4,344,758 | 8/1982 | Wielhouwer et al. ................... 433/137 |
| 4,626,211 | 12/1986 | Coston .................................... 433/137 |
| 4,701,129 | 10/1987 | Hazard .................................... 433/136 |
| 4,859,184 | 8/1989 | Hazard .................................... 433/136 |
| 4,889,490 | 12/1989 | Jenkinson ................................. 433/136 |
| 4,969,473 | 11/1990 | Bothwell . |
| 5,067,174 | 11/1991 | Ritchey et al. ................................. 2/9 |
| 5,140,997 | 8/1992 | Glassman ................................. 128/857 |
| 5,226,815 | 7/1993 | Bowman ................................. 433/137 |
| 5,551,087 | 9/1996 | Blutstein et al. ............................... 2/9 |
| 5,694,925 | 12/1997 | Reese et al. ........................ 128/206.19 |

Primary Examiner—Ralph A. Lewis
Attorney, Agent, or Firm—John D. Gugliotta

[57] ABSTRACT

Disclosed is a protective, disposable dental patient face mask that covers the patient's entire face, extending partially around the patient's head and secured by a pair of ear bands. A mouth aperture allows access to the patient's mouth and a nose mask that allows the patient to breathe freely while the air is filtered of impurities and flying debris. The face mask is constructed of a material that protects the patient's face from projected liquid and solid materials.

10 Claims, 4 Drawing Sheets

DENTAL PATIENT FACE MASK

BACKGROUND OF THE INVENTION

1. Field of the Invention

The present invention relates generally to dental accessories, and more specifically to a disposable face shield for use during the administration of dental procedures that protects the face from liquid and solid debris that is splattered and otherwise thrown about during the procedures.

2. Description of the Related Art the administration of dental procedures often produces a splattering or throwing about of liquid and solid materials from the patient's mouth. Caused by drilling, cleaning, polishing and rinsing the teeth, these materials include water, saliva, tooth pastes, scraped plaque, removed tooth enamel, amalgam filling material and a variety of other related substances. Quite often, these materials end up on the patients face and in their hair, on clothing, eyeglasses, etc., causing discomfort and making it necessary to wash after the procedures are completed. Furthermore, dentists and dental assistants or hygienists may also drop dental instruments, causing injury to their patients when the sharp points and edges come into contact with the patient's face. Accordingly, a need has been felt for a means by which dental patients can be protected from splattered liquid and solid substances as well as dropped instruments during the administration of dental procedures. The present invention fulfills this need by providing a protective, disposable dental patient face mask that covers the patient's entire face, extending partially around the patient's head and having an aperture through which the patient's mouth can be accessed by dental personnel.

A search of the prior art did not disclose any patents that read directly on the claims of the instant invention. However, several references to protective head and face shielding devices were discovered. These devices neither anticipate nor disclose any embodiment that would preclude the novelty and the utilitarian functionality of the features of the present invention.

The following patents describe a dental patient face and/or neck shield made of absorbent material:

U.S. Pat. No. 4,969,473, issued in the name of Bothwell;

U.S. Pat. No. 4,889,490, issued in the name of Jenkinson;

U.S. Pat. No. 4,626,211, issued in the name of Coston;

U.S. Pat. No. 4,344,758, issued in the name of Wielhouwer et. al.;

U.S. Pat. No. 3,478,432, issued in the name of Gross; and

U.S. Pat. No. 2,564,952, issued in the name of Blasius.

The Bothwell patent discloses a dental patient face and neck shield wherein a shroud covers the entire patient's head with the exception of the mouth area.

Including a pair of translucent sight apertures, the shield is constructed of an absorbent material that is intended to deflect solid objects and absorb liquids. This device, however, is inadequate due to the fact that the absorbent material will allow liquids to permeate the shield, coming into contact with the patient's face.

The Jenkinson, Coston, Wielhouwer et. al., Gross, and Blasius patents all disclose dental face shields that are designed to protect the area surrounding the mouth only, leaving, to varying degrees, the eyes, nose and face unprotected.

U.S. Pat. Nos. 4,859,184 and 4,701,129, both issued in the name of Hazard, describe a face shield device for protecting the wearer's eyes and face. These devices are not disposable in nature nor do they allow for access to the users mouth area. Neither disclosure anticipates a use for patient protection during dental procedures.

While several features exhibited within these references may be incorporated into this invention, alone and in combination with other elements, the present invention is sufficiently different so as to make it distinguishable over the prior art.

SUMMARY OF THE INVENTION

The present invention consists of a protective, disposable dental patient face mask that covers the patient's entire face, extending partially around the patient's head and secured by a pair of ear bands. A mouth aperture allows access to the patient's mouth so that dental procedures can be performed while protecting the patient's face. The face mask includes a molded nose mask that is contoured to match the shape of a typical nose so as to rest comfortably thereon. The face mask is constructed of a three-ply material having a waterproof inner layer sandwiched between two absorbent outer layers. The outer layer that rests against the face of the patient is constructed of a hypo-allergenic material. The nose mask is constructed of an air permeable filtering material that allows the patient to breathe freely while the air is filtered of impurities and flying debris. A variety of features are included so as to fit the specific needs and/or desires of either the dental personnel or patient. These options include a translucent window that allows the patient to see through the face mask and a perforated upper portion that allows for removal of the face mask along a line just below the eyes.

It is therefore an object of the present invention to provide a dental patient face mask that protects the patient's face from liquids and solids projected from the patient's mouth during the administration of dental procedures.

It is another object of the present invention to provide a dental patient face mask that allows complete and unobstructed access to the patients mouth, teeth and gums during the administration of dental procedures.

It is another object of the present invention to provide a dental patient face mask that is disposable, thereby promoting a safe and sanitary application.

It is another object of the present invention to provide a dental patient face mask that includes a nose mask portion that allows the patient to breathe freely there through.

It is another object of the present invention to provide a dental patient face mask that is constructed of a three-ply material having a waterproof inner layer sandwiched between two absorbent outer layers.

It is another object of the present invention to provide a dental patient face mask wherein the outer layer that rests against the face of the patient is constructed of a hypo-allergenic material.

It is another object of the present invention to provide a dental patient face mask that will absorb liquids and deflect solids.

It is another object of the present invention to provide a dental patient face mask that includes a transparent sight aperture that allows the patient to see through the mask.

It is another object of the present invention to provide a dental patient face mask that includes a removable upper portion that allows the mask to cover only the area surrounding the patient's mouth during procedures that are unlikely to project materials further than the extent of the mask.

Finally, It is an object of the present invention to provide a dental patient face mask that is both cost-effective and easy to manufacture.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

LIST OF REFERENCE NUMBERS

| | |
|---|---|
| 10 Face Mask | 25 Ear Bands |
| 11 Masking Sheet | 30 Perforation Line |
| 12 Molded Nose Mask | 31 Lower Protection Portion |
| 13 Sight Aperture | 32 Upper Protection Portion |
| 14 Mouth Cut-Out | 40 Soft Nose Mask |
| 15 Nose Bridge Piece | 41 Support Band |
| 16 Rolled Lower Border | 42 Perimeter Support Band |
| 20 Translucent Plastic Material | |
| 21 Glued Seam | |

DESCRIPTION OF THE PREFERRED EMBODIMENTS

1. Detailed Description of the Figures

Figure 1:
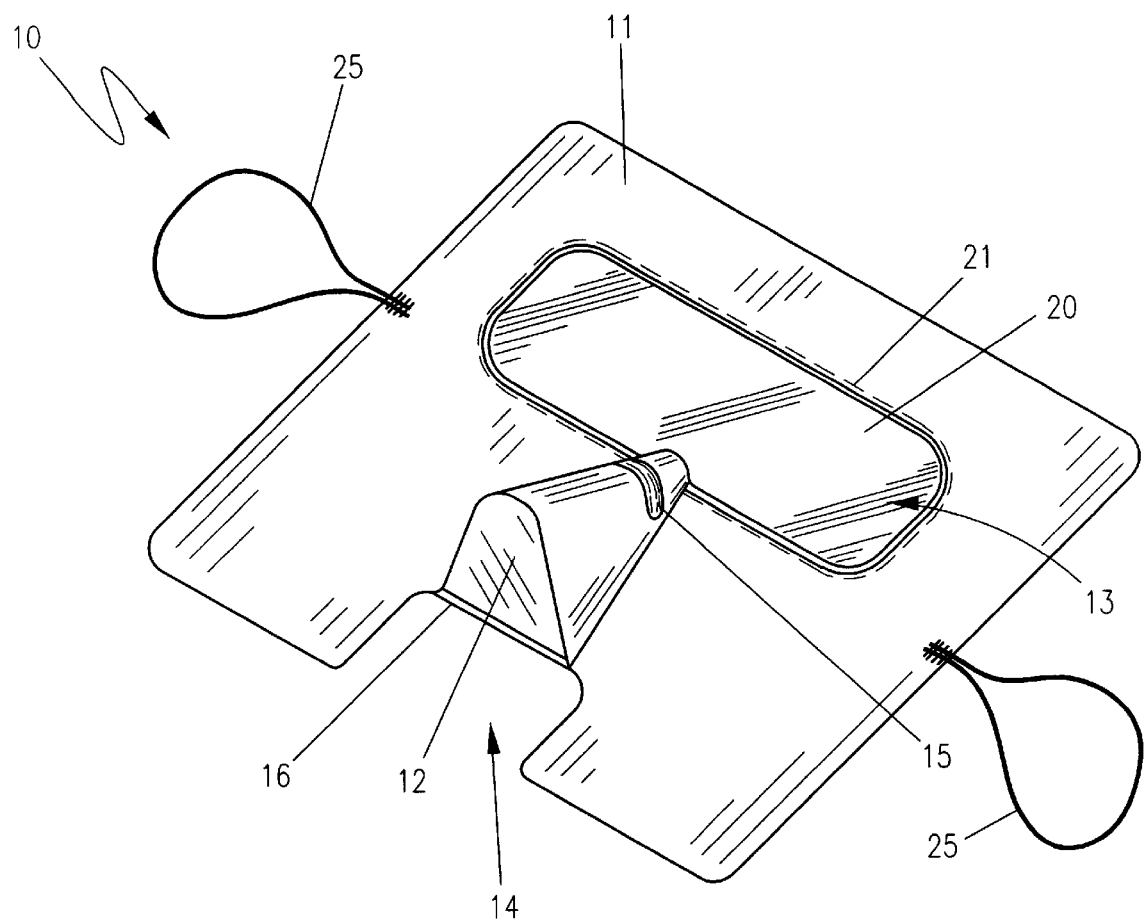
FIG. 1 is a perspective view of the dental patient face mask having a molded nose mask and a sight aperture, according to the preferred embodiment of the present invention.
Figure 2:
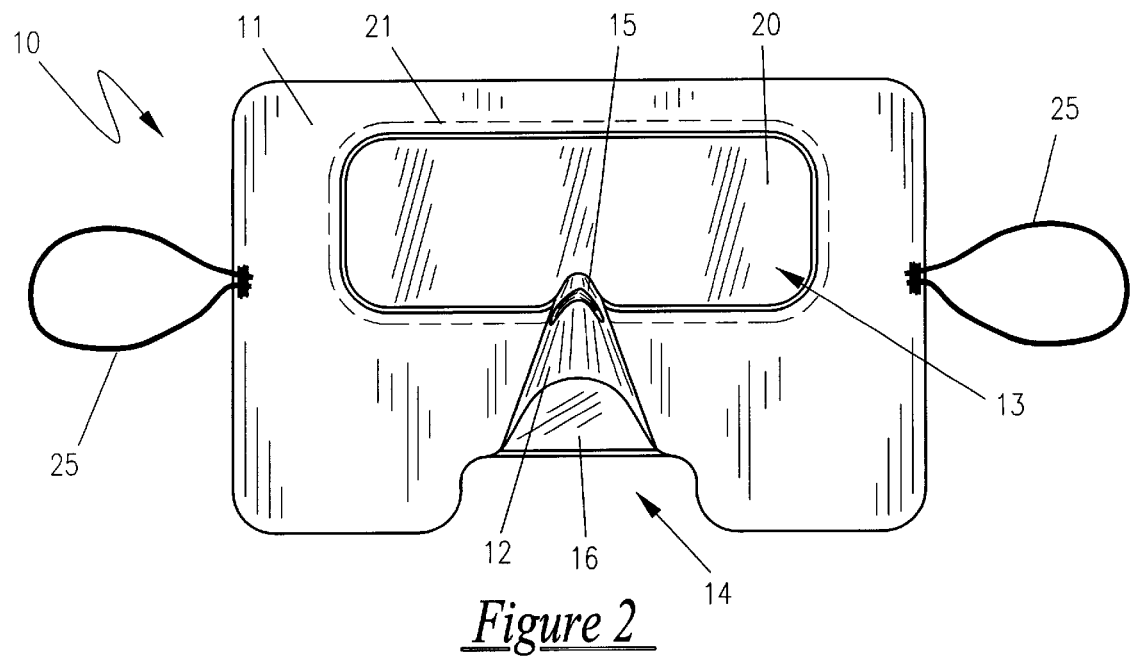
FIG. 2 is a front view of the dental patient face mask having a molded nose mask and a sight aperture, according to the preferred embodiment of the present invention.

Referring now to FIGS. 1–2, depicted is the dental patient face mask, hereinafter face mask 10, according to the preferred embodiment of the present invention. Protecting a dental patient (not shown in the Figures) from liquids and solids often projected during dental procedures, the face mask 10 consists of a masking sheet 11 that includes a molded nose mask 12, a sight aperture 13 and a mouth cut-out 14.

The masking sheet 11 is preferably of a three-ply material having a waterproof inner layer sandwiched between two absorbent outer layers (not shown in the Figures). The outer layer that rests against the face of the patient is constructed of a hypo-allergenic material. The absorbent layers serve to absorb liquids projected from the mouth of the patient or from dental instruments and deflects solid materials while the waterproof layer isolates the patient's face from the absorbed liquids.

The molded nose mask 12 is constructed of a generally rigid cotton fiber material that maintains a concave shape that will accept the patient's nose. The cotton fiber material is air permeable, allowing the patient to breathe freely through is the nose while simultaneously filtering the air and protecting the nose from projected liquids and solids. Although cotton fiber material is the preferred material, it is realized that other equally suitable materials such as a sponge filtering material may be used to produce the desired results. The molded nose mask 12 includes a nose bridge piece 15 that allows the molded nose mask 12 to be fitted to the patient's nose, providing a secure custom fit. The nose bridge piece 15 is constructed of a thin metal foil material that can be pressed against the patient's nose, bending to match the contour thereof and maintaining that shape so as to create a friction fit between the molded nose mask 12 and the patient's nose. A rolled lower border 16 of the molded nose mask 12 provides a tight, secure fit with the curved area between the upper lip and nose of the patient.

The sight aperture 13 consists of an elongated hole cut in the masking sheet 11, above the molded nose mask 12 so as to coincide with the patient's eyes when the face mask 10 is being worn. The sight aperture 13 is filled with a translucent plastic material 20 that is attached to the masking sheet 11 via a glued seam 21 or other suitable fastening or adhesive materials. The translucent plastic material 20 incorporated into the construction of the sight aperture 13 allows the patient to see through the face mask 10 during the administration of dental procedures while protecting the eyes and surrounding areas from projected materials.

The mouth cut-out 14 allows the face mask 10 to rest upon the patient's face with the masking sheet 11 surrounding the upper lip/mouth while allowing complete and unobstructed access to the patient's mouth, teeth and gums. Placed on the patient's face with the nose mask 12 covering the patient's nose, the sight aperture 13 placed over the eyes and secured thereto by the nose bridge piece 15 in conjunction with a pair of elastic ear bands 25 placed around the patient's ears, the face mask provides protection of the patient's face from liquid and solid debris, as well as dropped dental instruments and other materials, while allowing the patient to see and breathe freely.

Figure 3:
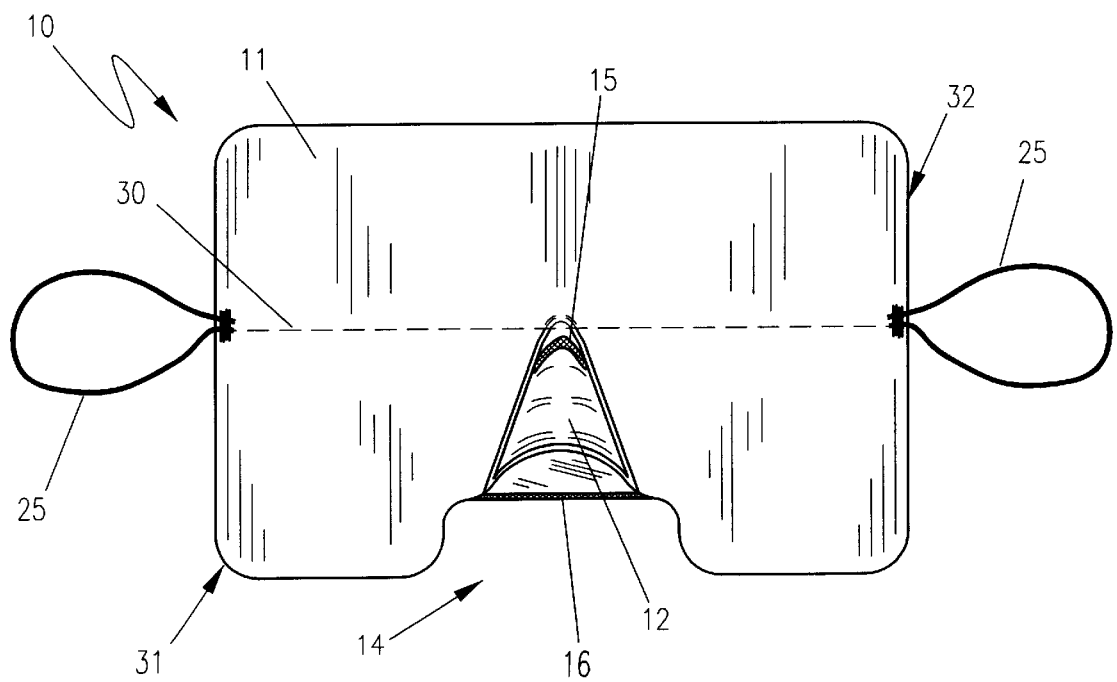
FIG. 3 is a front view of the dental patient face mask having a molded nose mask and a removable upper face portion, according to an alternate embodiment of the present invention.

Referring now to FIG. 3, depicted is a first alternate embodiment of the present invention wherein the sight aperture 20 is eliminated from the face mask 10, prohibiting the patient from seeing through the masking sheet 11, but producing an equally protective design that is less costly and easier to produce. It is envisioned that under the present teachings it would be obvious to one skilled in the art to include a means of providing transparent or translucent material across the sigh aperture 20. In such an instance, a tinging means could be easily incorporated to provide additional comfort to the eyes of the user. It should be noted that, in this first alternate embodiment, the face mask 10 is identical in design and function to that of the preferred embodiment and, as such, retains the utilitarian functionality thereof minus, of course, that of the sight aperture 13.

Also included in this first alternate embodiment is a perforation line 30 that defines the boundary between the lower protection portion 31 and the upper protection portion 32 of the face mask 10. In situations where the patient is uncomfortable having their eyes covered, the upper protection portion 32 can be removed by tearing it off along the perforation line 30. In doing so, the patient may desire to wear glasses or goggles to provide protection for their eyes. Having the upper protection portion 32 removed, the lower protection portion 31 remains, shielding the nose, cheeks and area surrounding the mouth as described herein above.

Figure 4:
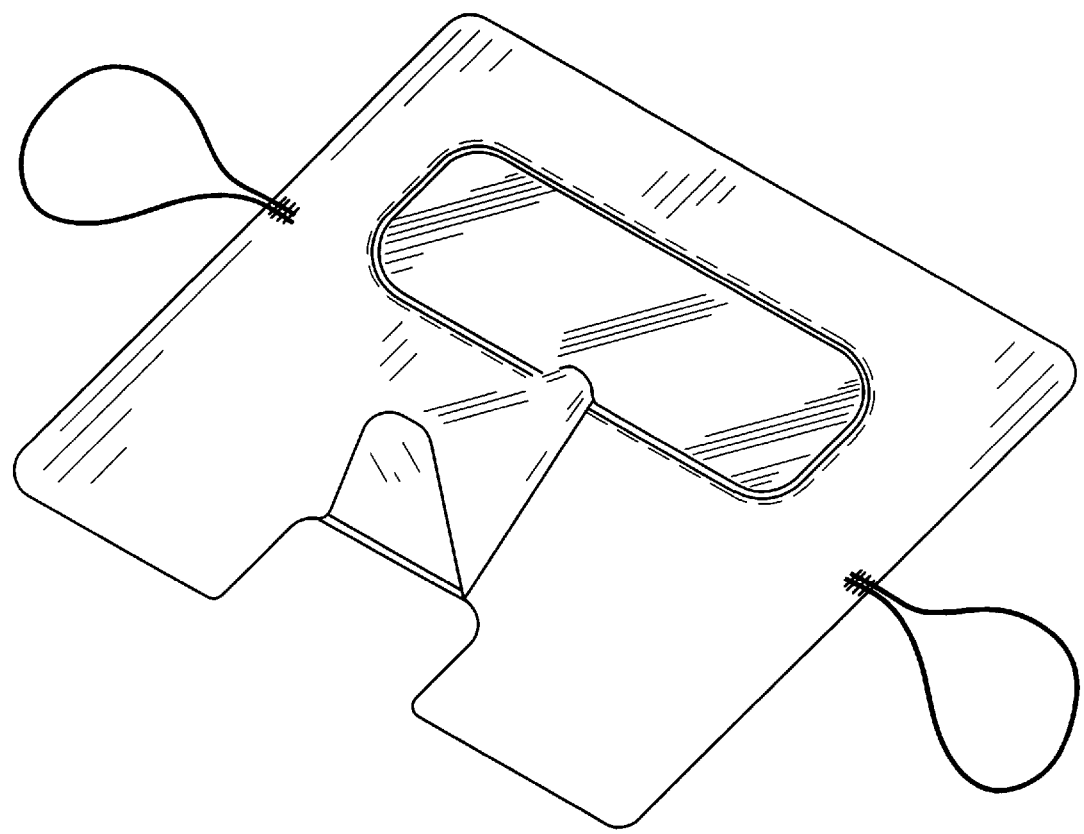
FIG. 4 is a perspective view of the dental patient face mask having a non-molded soft nose mask and a sight aperture, according to an alternate embodiment of the present invention.
Figure 5:
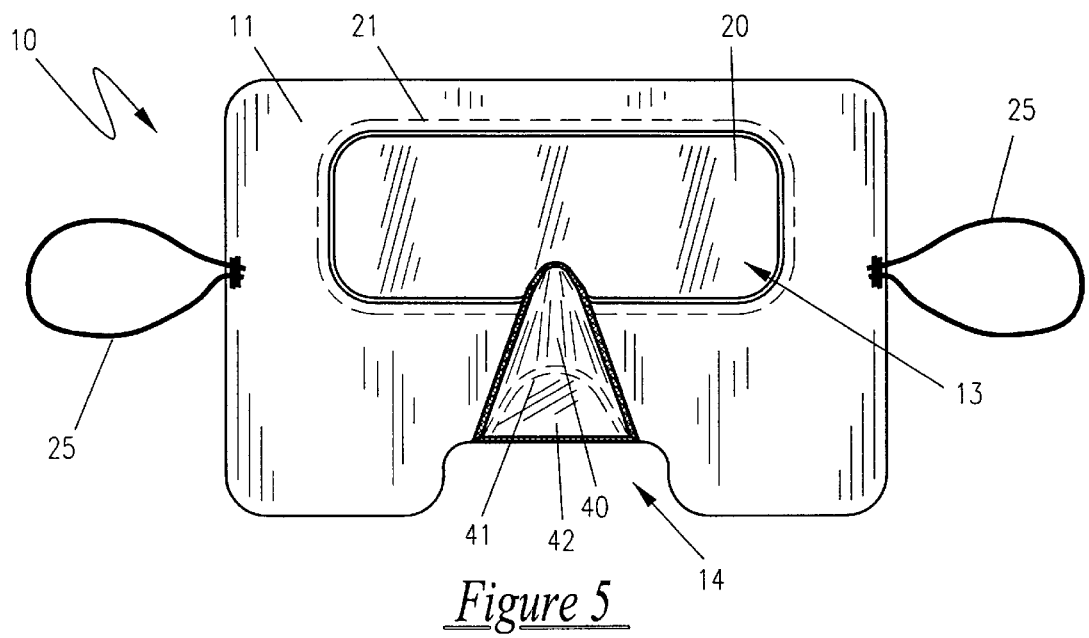
FIG. 5 is a front view of the dental patient face mask having a non-molded soft nose mask and a sight aperture, according to an alternate embodiment of the present invention.

Referring now to FIG. 4–5, depicted is a second alternate embodiment of the present invention wherein the molded nose mask 12 is replaced with a soft nose mask 40, attached to the face mask 10. The incorporation of the soft nose mask 40, is intended to allow for the use of alternative materials that may be more effective as a filtering device as well as providing an equally protective design that is less costly and easier to produce. It should be noted that, in this second alternate embodiment, the face mask 10 is identical in design and function to that of the preferred embodiment and, as such, retains the utilitarian functionality thereof, replacing the molded nose mask 12 with the soft nose mask 40.

The soft nose mask 40 is constructed of a generally soft and flexible cotton fiber material that forms a concave shape supported by a support band 41 constructed of a generally rigid cardboard material or the like. Although the incorporation of the support band 41 is desirable, it is realized that its use may not be necessary and could be omitted, if necessary. As with the molded nose mask 12, the cotton fiber material is air permeable, allowing the patient to breathe freely through the nose while simultaneously filtering the air and protecting the nose from projected liquids and solids. Although cotton fiber material is the preferred material, it is realized that other equally suitable materials such as a sponge filtering material may be used to produce the desired results. The soft nose mask 40 is supported about its perimeter by a perimeter support band 42 that conforms with the contour of the patient's face when pressed against it, forming a tight seal and aiding in supporting the face mask. The perimeter support band 42 is constructed of a thin metal foil material that can be pressed against the patient's nose, bending to match the contour thereof and maintaining that shape so as to create a friction fit between the soft nose mask 40 and the patient's nose.

Figure 6:
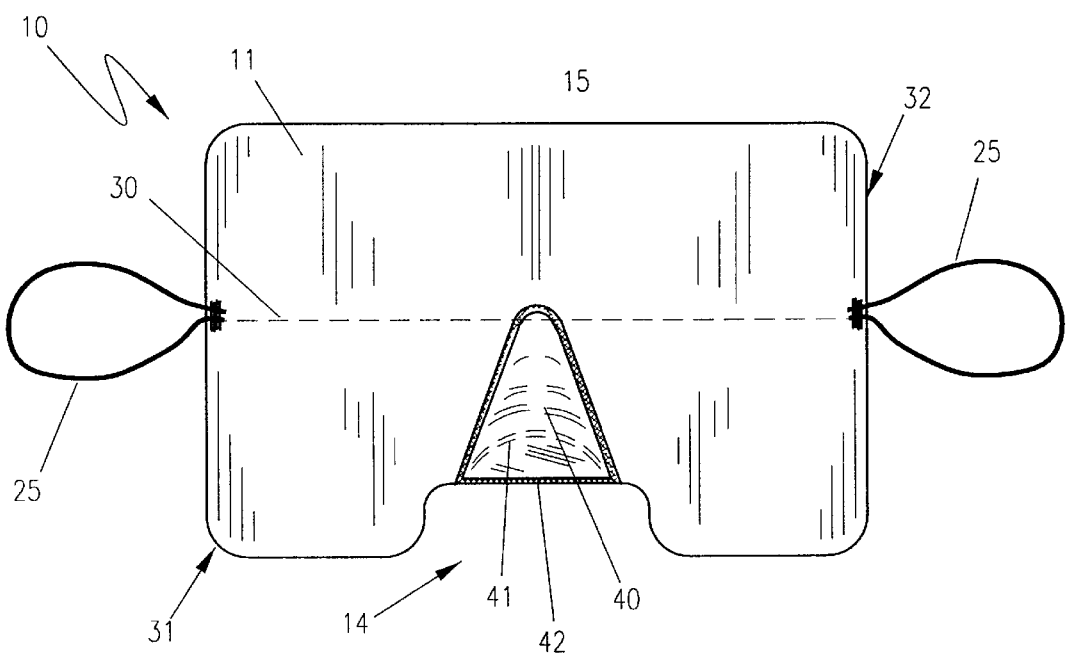
FIG. 6 is a front view of the dental patient face mask having a non-molded soft nose mask and a removable upper face portion, according to an alternate embodiment of the present invention.

Referring now to FIG. 6, depicted is a third alternate embodiment of the present invention wherein the sight aperture 20 is eliminated from the face mask 10 having the soft nose mask 40 as depicted in the second alternate embodiment, prohibiting the patient from seeing through the masking sheet 11, but producing an equally protective design that is less costly and easier to produce. It should be noted that, in this third alternate embodiment, the face mask 10 is identical in design and function to that of the second alternate embodiment and, as such, retains the utilitarian functionality thereof minus, of course, that of the sight aperture 13.

Also included in this third alternate embodiment is a perforation line 30 that defines the boundary between the lower protection portion 31 and the upper protection portion 32 of the face mask 10. In situations where the patient is uncomfortable having their eyes covered, the upper protection portion 32 can be removed by tearing it off along the perforation line 30. In doing so, the patient may desire to wear glasses or goggles to provide protection for their eyes. Having the upper protection portion 32 removed, the lower protection portion 31 remains, shielding the nose, cheeks and area surrounding the mouth as described herein above.

2. Operation of the Preferred Embodiment

In accordance with the preferred embodiment of the present invention and as shown in the Figures, the face mask 10 is attached to the patient's face in the same manner, regardless of whether the preferred or one of the alternate embodiments are being used. The face mask 10 is placed over the patient's face, the masking sheet 11 laying around the sides of the patient's face and is attached thereto by the ear bands 25. In the preferred embodiment and first alternate embodiment, the nose bridge piece 15 is pressed against the patient's nose, conforming the nose bridge piece 15 to the contour of the patient's nose and securing it thereto. In the second alternate embodiment and third alternate embodiment, the perimeter support band 42 is pressed against the patient's nose, conforming the perimeter support band 42 to the contour of the patient's nose and securing it thereto. In the case of the preferred and second alternate embodiments, the patient is afforded the ability to observe their surroundings through the sight aperture 13. In the case of the first and third alternate embodiments, the patient has the option of removing the upper protective portion 32 of the masking sheet 11, allowing the patient the ability to observe their surroundings. In all of the embodiments, use of the face mask 10 protects the patient from projected liquid and solid materials often associated with many dental procedures.

While the preferred embodiments of the invention have been shown, illustrated, and described, it will be apparent to those skilled in this field that various modifications may be made in these embodiments without departing from the spirit of the present invention. It is for this reason that the scope of the invention is set forth in and is to be limited only by the following claims.

What is claimed is:

1. A dental patient face mask comprising:

a generally rectangular masking sheet having an upper edge opposite a lower edge, a left edge opposite a right edge and an exterior surface opposite an interior surface;

a mouth aperture centered along said bottom edge, said mouth aperture comprising a generally arcuate cutout portion of said masking sheet;

a nose mask having a generally rounded triangular shape and contoured so as to form a hollow interior space defining a nose receiving cavity, said nose mask attached to said exterior surface of said masking sheet, protruding therefrom, said nose mask positioned centered upon and adjacent to said mouth aperture, said masking sheet being cutout along the perimeter of said nose mask and exposing said nose receiving cavity; and a left ear band attached to said left edge and a right ear band attached to said right edge, said left and right ear bands having a generally elastic quality and positioned in a location generally equal to that of the upper edge of said nose mask;

wherein said dental patient face mask is secured to a patient's face, said masking sheet placed over said patient's face, said nose receiving cavity accepting said patient's nose, said mouth aperture lying along the edge of said patient's upper lip and said left and right edges laying around said patient's face, said left and right ear bands fitting around said patient's ears, said dental patient face mask protecting said patient from projected liquid and solid materials often encountered during the administration of dental procedures.

2. The dental patient face mask of claim 1, wherein said masking sheet further comprises a three-ply material having a waterproof inner layer sandwiched between interior and exterior outer layers, said interior outer layer being of an absorbent nature and constructed of a hypo-allergenic material and said exterior outer layer being constructed of an absorbent material.

3. The dental patient face mask of claim 2, wherein said nose mask further comprises a generally rigid, molded air permeable membrane construction wherein said patient is permitted to breathe therethrough, said molded air permeable membrane filtering air as said patient breathes.

4. The dental patient face mask of claim 3, wherein said nose mask further comprises a nose bridge piece comprising a bendable metal strip, said nose bridge piece secured to said molded air permeable membrane such that, when pressed against said patient's nose, said nose bridge piece conforms to the contour of said patient's nose, creating a friction fit therewith that stabilizes said dental patient face mask.

5. The dental patient face mask of claim 4, wherein a sight aperture is located above said nose mask, said sight aperture comprising an elongated aperture in said masking material creating fluid connectivity between said exterior surface and said interior surface, said sight aperture having a translucent plastic material spanning the area thereof and attached to said masking material, whereby said patient can see through said sight aperture while wearing said dental patient face mask.

6. The dental patient face mask of claim 4, wherein said masking sheet further comprises a perforation line positioned perpendicular to and spanning between said left and right edges, said perforation line having a position generally near the upper edge of said nose mask, facilitating the easy removal of said masking material above said patient's nose, thus providing said patient with unobstructed view.

7. The dental patient face mask of claim 2, wherein said nose mask further comprises a generally flexible air permeable membrane construction wherein said patient is permitted to breathe therethrough, said flexible air permeable membrane filtering air as said patient breathes and having an interior support member attached thereto that supports said flexible air permeable membrane in a position forming said nose receiving cavity.

8. The dental patient face mask of claim 7, wherein said nose mask further comprises a perimeter support piece comprising a bendable metal strip, said perimeter support piece secured to said flexible air permeable membrane about the perimeter thereof such that, when pressed against said patient's face, said perimeter support piece conforms to the contour of said patient's face, creating a friction fit therewith that stabilizes said dental patient face mask.

9. The dental patient face mask of claim 8, wherein a sight aperture is located above said nose mask, said sight aperture comprising an elongated aperture in said masking material creating fluid connectivity between said exterior surface and said interior surface, said sight aperture having a translucent plastic material spanning the area thereof and attached to said masking material, whereby said patient can see through said sight aperture while wearing said dental patient face mask.

10. The dental patient face mask of claim 8, wherein said masking sheet further comprises a perforation line positioned perpendicular to and spanning between said left and right edges, said perforation line having a position generally near the upper edge of said nose mask, facilitating the easy removal of said masking material above said patient's nose, thus providing said patient with unobstructed view.

* * * * *